US00PP34812P2

(12) United States Plant Patent
Wang

(10) Patent No.: US PP34,812 P2
(45) Date of Patent: Dec. 13, 2022

(54) ***ACTINIDIA* PLANT NAMED 'YNRT-1'**

(50) Latin Name: *Actinidia valvata*
Varietal Denomination: YNRT-1

(71) Applicant: Zhongyan Wang, Hunan (CN)

(72) Inventor: Zhongyan Wang, Hunan (CN)

( * ) Notice: Subject to any disclaimer, the term of this patent is extended or adjusted under 35 U.S.C. 154(b) by 0 days.

(21) Appl. No.: 17/548,966

(22) Filed: Dec. 13, 2021

Related U.S. Application Data

(60) Provisional application No. 63/128,831, filed on Dec. 21, 2020.

(51) Int. Cl.
*A01H 6/00* (2018.01)
*A01H 5/08* (2018.01)

(52) U.S. Cl.
USPC ..... Plt./156

(58) Field of Classification Search
USPC ..... Plt./156
CPC ..... A01H 6/00; A01H 5/08
See application file for complete search history.

*Primary Examiner* — Keith O. Robinson
(74) *Attorney, Agent, or Firm* — Penny J. Aguirre

(57) ABSTRACT

A new cultivar of *Actinidia* plant named 'YNRT-1' that is characterized by its strong, vigorous growth habit, its good growth in wet and waterlogged soil, its resistance to *Pseudomonas syringae* pv. *actinidiae* (PSA), and its lack of fruit production as it is a male cultivar.

2 Drawing Sheets

Botanical classification: *Actinidia valvata.*
Varietal denomination: 'YNRT-1'.

BACKGROUND OF THE INVENTION

The present invention relates to a new and distinct cultivar of *Actinidia valvata* and will be referred to hereafter by its cultivar name, 'YNRT-1'. The new cultivar represents a new kiwi plant that is grown for use in the fresh fruit market.

The new cultivar was derived from an ongoing controlled breeding program conducted by the Inventor in Changsha, Hunan, China with objectives of developing new and superior cultivars of *Actinidia valvata* that have strong growth and vigor and are therefore suitable to use as a rootstock for *Actinidia chinensis*. The new cultivar arose as a seedling from seed collected from an open pollinated an unnamed and unpatented plant of *Actinidia valvata* in 2010. The male parent is therefore unknown. 'YNRT-1' was selected as a single unique plant amongst the seedlings evaluated in 2015.

Asexual propagation of the new cultivar was first accomplished by hardwood stem cuttings in Changsha, Hunan, China by the Inventor in 2015. Asexual propagation by hardwood stem cuttings has been determined that the characteristics of this cultivar are stable and are true to type in successive reproductions.

SUMMARY OF THE INVENTION

The following traits have been repeatedly observed and represent the characteristics of the new cultivar. These attributes in combination distinguish 'YNRT-1' as a new and unique cultivar of *Actinidia.*

1. 'YNRT-1' exhibits a strong, vigorous growth habit.
2. 'YNRT-1' exhibits good growth in wet and waterlogged soil.
3. 'YNRT-1' exhibits resistance to *Pseudomonas syringae* pv. *actinidiae* (PSA).

4. 'YNRT-1' exhibits no fruit production as it is a male cultivar.

The female parent of 'YNRT-1' differs from 'YNRT-1' in having a much less vigorous growth habit. 'YNRT-1' can also be compared to *Actinidia* cultivars 'MiLiang-1' (not patented) and 'Cuiyu' (not patented). 'MiLiang-1' and 'Cuiyu' are both similar to 'YNRT-1' in being used as kiwifruit rootstock. 'MiLiang-1' differs from 'YNRT-1' in being a female cultivar and in having very thick leaves and a more vigorous growth habit, and in not being tolerant to waterlogging. 'Cuiyu' differs from 'YNRT-1' in being a female cultivar, in having thick leaves, and in not being tolerant to waterlogging.

BRIEF DESCRIPTION OF DRAWING

The accompanying colored photograph illustrate the overall appearance and distinct characteristics of the new *Actinidia.*

The photograph in FIG. 1 was taken of a 2-year-old plant of the new cultivar as grown indoors under low light in a 1-gallon container in a greenhouse in Saskatoon, Saskatchewan, Canada and removed from its container for the photograph. The photograph in FIG. 1 provides a view of the roots of 'YNRT-1'.

Figure 1:
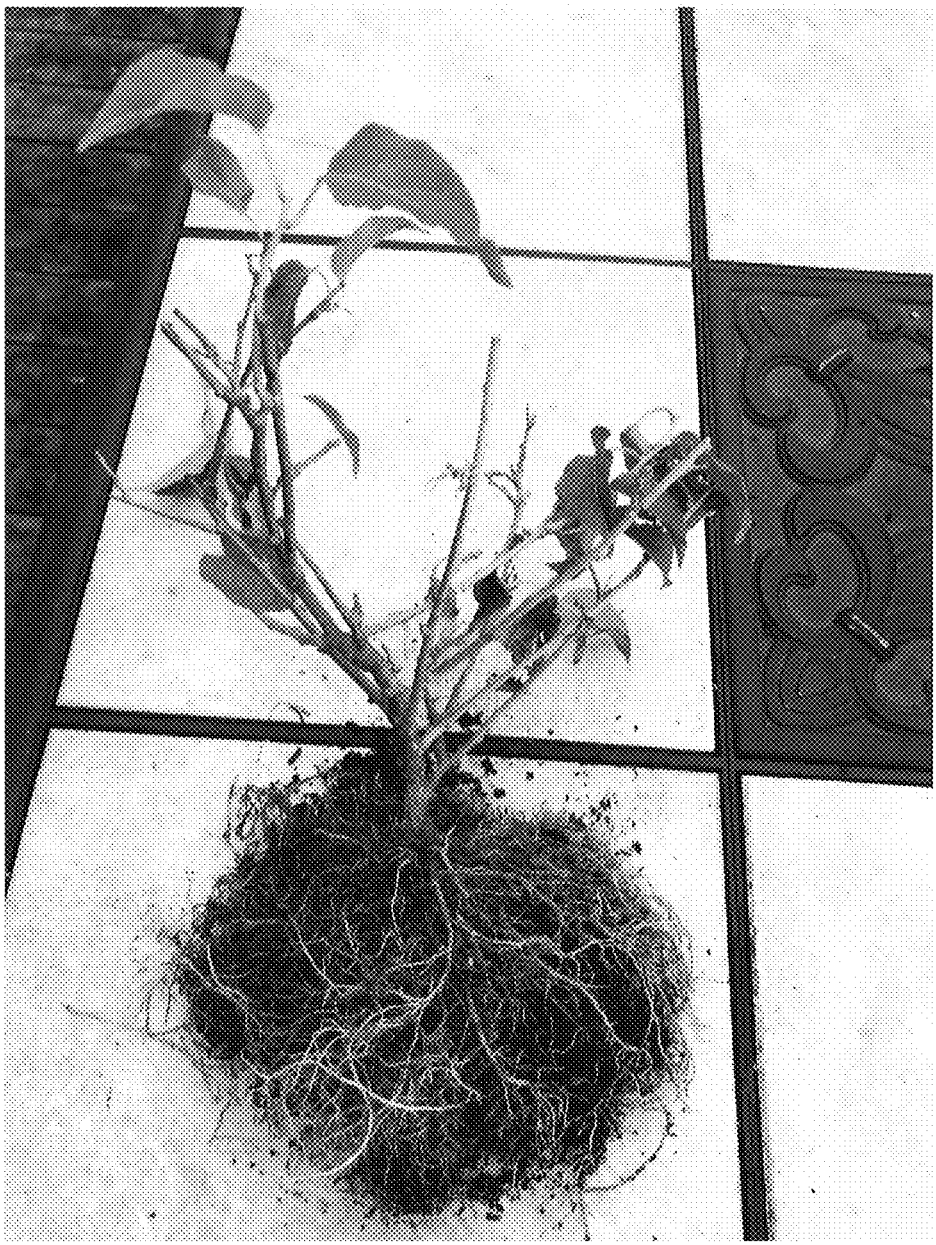
Figure 2:
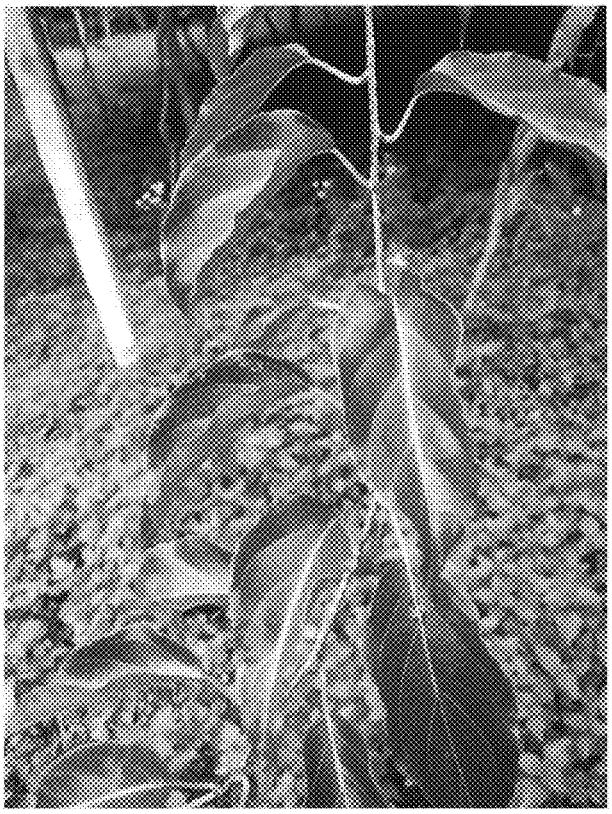
Figure 3:
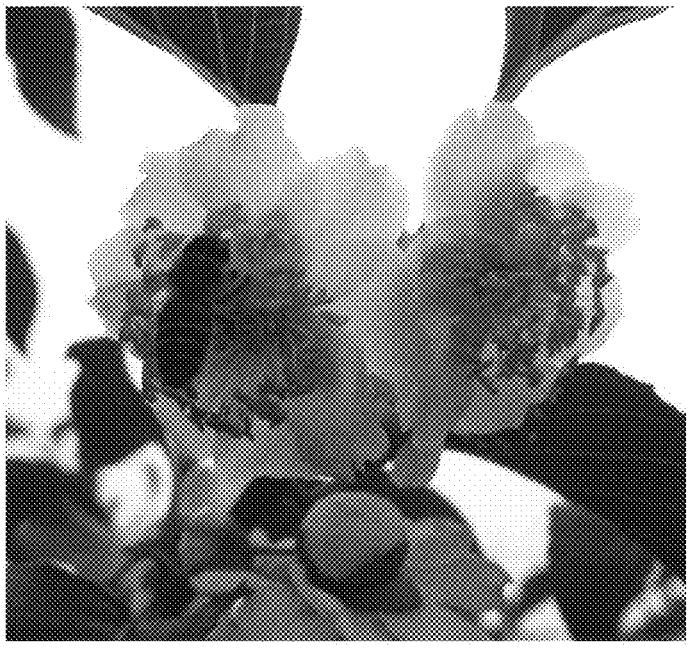

The photograph in FIG. 2 and FIG. 3 was taken of 2-year-old plants of 'YNRT-1' as grown in Changsha, Hunan, China. The photograph in FIG. 2 provides a view of the stem and leaves of 'YNRT-1'. The photograph in FIG. 3 provides a view of flowers of 'YNRT-1'.

The colors in the photograph are as close as possible with the photographic and printing technology utilized and the color values cited in the detailed botanical description accurately describe the colors of the new *Actinidia.*

DETAILED BOTANICAL DESCRIPTION OF THE PLANT

The following is a detailed description of 2-year-old plants of the new cultivar as grown indoors under low light in containers in a greenhouse in Saskatoon, Saskatchewan, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Deciduous vine.

*Plant habit*.—Climbing.

*Blooming period*.—5 to 7 days in late April in China.

*Plant size*.—An average of 3 m in height and 8 m in spread for an eight year-old plant.

*Growth rate*.—Moderate.

*Diseases and pests*.—Highly resistant to bacterial canker caused by *Pseudomonas syringae* pv. *actinidiae* (PSA), no susceptibility or resistance to pests has been observed.

*Hardiness*.—At least in U.S.D.A. Zone 6 to 9.

*Root description*.—Fibrous, 197A and 199A in color.

*Propagation*.—Hardwood stem cuttings.

*Root development*.—Roots initiate in an average of 1 month, 3 to 5 months to produce a young plant from a rooted cutting.

Branch description:

*Branch strength*.—Strong.

*Branch surface*.—Young branches; glossy, rugose and moderately covered with lenticles vertical in orientation, 1 mm in length, 0.5 mm in width, quantity per 1 cm diameter area is an average of 10, 145D and flushed with 175A in color, density of hairs on young shoots is very sparse, mature branches; matte, rugose and moderately covered with lenticles rounded in shape, 1 mm in diameter, quantity per 1 cm diameter area is an average of 10, 165B in color, old wood; matte and rugose.

*Branch size*.—An average of 2.5 m in length and 1 to 3 mm in diameter (thin) as a one-year-old shoot.

*Internode length*.—An average of 2 cm.

*Branch color*.—Young; 145A, mature; 197A, old wood; 199A and N199B.

*Branch shape*.—Flattened to oval in shape.

*Branch bud cover*.—Present, size of bud cover is small.

*Branch bud support*.—Medium.

*Branch pith*.—Solid.

Foliage description:

*Leaf orientation*.—Upward to outward with aspect slightly cupped inward.

*Leaf division*.—Simple.

*Leaf shape*.—Cuneate.

*Leaf arrangement*.—Alternate.

*Leaf size*.—Average of 6.5 cm in length and 3.5 cm in width.

*Leaf apex*.—Acuminate.

*Leaf base*.—Cuneate, leaf lobes primarily absent but when present they are far apart.

*Leaf surface*.—Upper and lower surface glossy, young and mature upper surface very sparsely covered with strigose hairs mainly close to the outside edges of the leaf, an average of 0.05 mm in length, NN155D in color, young and mature lower surface glabrous.

*Leaf margin*.—Spiny, NN155D in color spacing on margins 1 to 2 mm intervals around the leaf.

*Leaf color*.—Upper surface; a blend of 144A and 143A, lower surface; 144A.

*Leaf venation*.—Cross-venulate, upper and lower surface; glabrous, slightly translucent, 145A in color, sometimes has strigose hairs on center vein, 0.05 mm in length, NN155A in color.

*Petiole*.—Average of 1.5 cm in length, 1.5 mm in width, surfaces; glabrous, slightly glossy, flattened in shape, 180A in color.

Flower description:

*Flowering period*.—5 to 7 days in late April in China.

*Inflorescence type*.—Single or cyme.

*Inflorescence size*.—Average of 4 cm in length when 2-flowered.

*Number of flowers*.—1 to 3 per inflorescence.

*Flower size*.—An average of 1.5 cm in depth and 2 cm in diameter.

*Flower type*.—Rotate.

*Flower buds*.—Globose (slightly oblong) in shape, 155B in color with sepal base 144A, average of 1 cm in length and 1.2 cm in diameter, glabrous surface.

*Flower fragrance*.—None detected.

*Flower aspect*.—Outward from stem.

*Petals*.—7 to 9 per flower, unfused and overlapping, rounded and ruffled apex, truncate base, margin entire and slightly undulated, average of 1.4 cm in length and 1.2 cm in width, color of upper and lower surface when opening and mature 144B.

*Sepals*.—3 per flower, overlapping at base, broadly ovate in shape, broadly acute apex, truncate-cuneate base, entire margin, average of 7 mm in length and width, color 144B on upper and lower surface, glabrous on both surfaces.

*Peduncle* (*single flowers or cyme*).—144A in color, average of 1.5 cm in length and 2 mm in width, sparsely pubescent surface.

*Pedicel* (*on cyme if present*).—An average of 8 mm in length and 1.5 mm in width, 144A in color, sparsely pubescent surface.

Reproductive organs (male flowers only):

*Gynoecium*.—None, male flowers only.

*Androecium*.—Stamens; average of 50, filaments; 6 mm in length, 155C in color, anther; cylindrical in shape, 2 mm in length, 162B in color, pollen; none observed.

Fruit description: No fruit is produced as it is male cultivar.

It is claimed:

1. A new and distinct cultivar of *Actinidia* plant named 'YNRT-1' as described and illustrated herein.

* * * * *